United States Patent [19]

Eller

[11] Patent Number: 5,714,139
[45] Date of Patent: Feb. 3, 1998

[54] COMPOSITION AND ARTICLE FOR CONTROL OF THE PLUM CURCULIO

[75] Inventor: Fred J. Eller, Metamora, Ill.

[73] Assignee: The United States of America as represented by the Secretary of Agriculture, Washington, D.C.

[21] Appl. No.: 682,894

[22] Filed: Jun. 25, 1996

[51] Int. Cl.$^6$ ...................................... A01N 37/08
[52] U.S. Cl. ........................................ 424/84; 514/572
[58] Field of Search .......................... 424/84; 514/572

[56] References Cited

U.S. PATENT DOCUMENTS 5,393,522  2/1995  Eller et al. ................................. 356/36

OTHER PUBLICATIONS

Booth, D.C.; Phillips, T.W.; Claesson, A.; Silverstein, R.M.; Lanier, G.N. and West, J.R. "Aggregation Pheromone Components of Two Species of *Pissodes* Weevils (Coleoptera: Curculionidae)." *Journal of Chemical Ecology*, vol. 9, No. 1, 1983, pp. 1–12.

Hobbs, P.D. and Magnus, P.D. "Synthesis of Optically Active Grandisol." *J. Am. Chem. Soc. Chem. Comm.* 1974, pp. 856–857.

Mori, K.; Tamada, S. and Hedin, P.A. "(−)−Grandisol, the Antipode of the Boll Weevil Pheromone, is Biologically Active." *Naturwissenschaften* 65 (1978), pp. 653–654.

Eller, F.J.; Bartelt, R.J.; Shasha, B.S.; Schuster, D.J.; Riley, D.G.; Stansly, P.A.; Mueller, T.F.; Shuler, K.D.; Johnson, B.; Davis, J.H. and Sutherland, C.A. "Aggregation Pheromone for the Pepper Weevil, *Anthonomus eugenii* Cano (Coleoptera: Curculionidae): Identification and Field Activity." *Journal of Chemical Ecology*, vol. 20, No. 7, 1994, pp. 1537–1555.

Eller, F.J. and Bartelt, R.J. "Grandisoic Acid, a Male–Produced Aggregation Pheromone from the Plum Curculio, *Conotrachelus nenuphar*." *Journal of Natural Products*, 1996, vol. 59, No. 4, pp. 451–453.

Prokopy, R.J.; Galarza, G. and Phelan, P.L. "Monitoring Plum Curculio in Orchards: New Hope for a More Effective Method." *1993 Mass. Fruit Growers Assoc.* pp. 70–76.

Ayer, W.A. and Browne, L.M. "The Transformation of Carvone into Racemic Grandisol." *Can. J. Chem.*, vol. 52, (1974), pp. 1352–1360.

Tumlinson, J.H.; Hardee, D.D.; Gueldner, R.C.; Thompson, A.C.; Hedin, P.A. and Minyard, J.P. "Sex Pheromones Produced by Male Boll Weevil: Isolation, Identification, and Synthesis." *Science* 1969, pp. 1010–1012.

*Primary Examiner*—John Pak
*Attorney, Agent, or Firm*—M. Howard Silverstein; Curtis P. Ribando; John D. Fado

[57] ABSTRACT

The compound 1-methyl-2-(1-methylethenyl)-cyclobutaneacetic acid (grandisoic acid) has been found to be useful as an aggregation pheromone for plum curculio weevils. Both male and female plum curculios are attracted to the compound, particularly to the (+)-1R,2S enantiomer. The plum curculio is a major pest of stone and pome fruits. When applied to the habit of these pests via a pheromone dispenser, the compound has utility as a monitoring and/or control agent.

10 Claims, No Drawings

COMPOSITION AND ARTICLE FOR CONTROL OF THE PLUM CURCULIO

BACKGROUND OF THE INVENTION

1. Field of the Invention

This invention relates to an aggregation pheromone for attracting male and female adults of the plum curculio, *Conotrachelus nenuphar*, and to an article comprising a dispenser and the aggregation pheromone.

The plum curculio, *Conotrachelus nenuphar* (Herbst) (Coleoptera: Curculionidae), is a major pest of stone and pome fruits east of the Rocky Mountains. It is responsible for decreased yields and lowered fruit quality (Chapman). The plum curculio is the only key apple pest for which there is no accurate, reliable, practical means for detecting its presence or estimating its density (LeBlanc, Whalon).

2. Description of the Prior Art

Currently, jarring (tapping branches over a cloth), is the most reliable adult monitoring technique for the plum curculio. However, jarring is generally not popular with growers, because it can damage trees and cause some apples to fall (LaFleur). The appearance of fresh egg-laying scars on developing fruit is a more convenient and less disruptive method for timing insecticide sprays (Prokopy), however, such scars are only detectable several weeks after plum curculios arrive in orchards, which may be too late to achieve optimal control (LeBlanc).

Male-produced pheromones have been identified for other economically important weevils in the family Curculionidae (Mayer) and have become useful for monitoring populations (Cross). For example, (+)-grandisol (2A, shown below) is the major component of the pheromone of the boll weevil, *Anthonomus grandis* Boheman (Coleoptera: Curculionidae) (Tumlinson, Hobbs). However, no pheromone has been previously reported for the plum curculio.

SUMMARY OF THE INVENTION

I have now discovered that plum curculio weevils can be attracted by applying to their habitat an effective amount of (+)-(1R,2S)-1-methyl-2-(1-methylethenyl)-cyclobutaneacetic acid, also referred to as grandisoic acid. The compound is an attractant for both male and female weevils in both its purified form and also when used in combination with the 1S,2R enantiomer, 1B.

In accordance with this discovery, it is an object of the invention to identify grandisoic acid as a compound useful for attracting male and female plum curculio weevils.

Another object of the invention is to employ grandisoic acid or mixtures of it with its 1S,2R enantiomer as an attractant for male and female plum curculio weevils.

A further object of the invention is to employ grandisoic acid or mixtures of the compound with its 1S,2R enantiomer as a monitoring or control agent for the plum curculio.

Other objects and advantages of this invention will become readily apparent from the ensuing description.

DETAILED DESCRIPTION OF THE INVENTION

Identification of grandisoic acid as an aggregation pheromone for the plum curculio, *Conotrachelus nenuphar* (Herbst) (Coleoptera: Curculionidae), was discovered by analyzing male and female volatile collections from weevils feeding on plums and apples. Both the single-brooded northern strain and the double-brooded southern strain, which are reported to be reproductively incompatible (Padula) were found to produce grandisoic acid. Comparisons of the GLC chromatograms of male and female volatile collections revealed only one sex-specific peak in males. The peak shape (i.e., fronting) associated with this compound was reminiscent of that seen for geranic acid isolated from male pepper weevils (Eller) and suggested that the compound may be a carboxylic acid. This was further supported because the male-specific compound could be removed from the hexane extract using 5% $Na_2CO_3$ and the original compound could be regenerated by acidifying the $Na_2CO_3$ extract with 10% HCl and partitioning into hexane.

The mass spectral peaks at m/z 68 and 108 suggested a cyclobutane ring, as occurs in (+)-grandisol [2A], the major component of the pheromone of the boll weevil, *Anthonomus grandis* Boheman (Coleoptera: Curculionidae) (Tumlinson, Hobbs). The ion at 168 was consistent with a molecular formula of $C_{10}H_{16}O_2$, and the male-specific compound was tentatively identified as 1A.

Neither 1A (the carboxylic acid analog of 2A), nor its enantiomer 1B, have been previously reported as natural products; although racemic 1 (1A plus 1B) and 1B by itself were previously reported as synthetic intermediates (Ayer, Mori Naturwissenschaften 1978).

Racemic 1 was synthesized as a standard for comparison. The male-derived compound and racemic 1 gave identical retention indices on two achiral GLC columns (1269 and 1290 on DB-1 and DB-5, respectively). The male-derived compound and racemic 1 also had identical mass spectra, and $^1H$ and $^{13}C$ NMR spectra, and these were consistent with previous data (Ayer, Zurfluh). The chemical shift data for racemic 1 were very similar to those reported for racemic grandisol [2] (Mori Tetrahedron 1978), with the exception of C-7 because of the different functionality.

The male-derived compound was reduced to the corresponding alcohol with $LiAlH_4$ and the retention indices were identical with those of racemic grandisol [2] on the achiral columns (1196 and 1219 on DB-1 and DB-5, respectively). The mass spectra of the reduced male-derived compound and racemic grandisol [2] were identical as well.

A chiral GLC column (CDX-B) did not separate 1A from 1B, but it did resolve racemic grandisol [2] into two peaks with retention indices of 1406 and 1412, respectively. After reduction to the alcohol, the male-specific compound (from both the southern and northern strains of plum curculios) produced only a single peak, with a retention index of 1406. Thus, both strains produce just one enantiomer, and this was identical in retention index to (+)-grandisol [2A] (derived from male boll weevils) (Tumlinson, Hobbs). The retention index of synthetic (−)-grandisol [2B] was confirmed to be 1412.

Further confirmation of the stereochemistry was that the male-derived compound was found to have an optical rotation of $[\alpha]_D$=+47.9 (c 0.00267, n-hexane), while Mori et al. (Mori Naturwissenschaften 1978) reported an optical rotation of $[\alpha]_D$=−49.3 (c 0.74, n-hexane) for (1S,2R)-1-methyl-2-(1-methylethenyl)-cyclobutaneacetic acid [1B]. All evidence thus supports the conclusion that the male-derived compound from plum curculios has the same ring stereochemistry as (+)-grandisol [2A](i.e., 1R,2S), and thus, the male-derived compound is (+)-(1R,2S)-1-methyl-2-(1-methylethenyl)-cyclobutaneacetic acid [1A].

The identification of grandisoic acid as the aggregation pheromone for the plum curculio has potential use by pest managers as a survey tool to replace jarring or searching for egg-laying scars. Such a monitoring tool could improve the integrated management of orchards and reduce pesticide usage on apples, peaches, plums, and cherries.

It may be possible to increase the sensitivity of traps baited with grandisoic acid in several ways. The presence of the antipode of (+)-grandisoic acid in the racemic mixture may render the mixture less active; this phenomenon has been shown for several insect species (Vite, Light). It is possible to separate the enantiomers of grandisoic acid from a racemic mixture by using quinine salts (Mori, Naturwissenschaften 1978). Thus, for purposes of this invention, it is contemplated to use the racemic mixture of grandisoic acid enantiomers, the purified (+)-(1R,2S) configuration, or any configurationally biased mixture in which the (+)-(1R,2S) configuration is present in an amount greater than the (−)-(1S,2R) configuration.

Host compounds may synergize the activity of the pheromone, as has been shown for other curculionid weevils, including boll weevils (Hardee, Dickens 1986, Dickens 1989) pine weevils (Booth), pea leaf weevils (Blight) and palm weevils (Oehlschlager). Although a pheromone attractant apparently plays a role in mate-finding for the plum curculio, stridulation plays a role as well (Mampe). The males of other curculionid weevils have been demonstrated to both stridulate (Hyder, Harman) and produce an aggregation pheromone (Booth, Roseland). It may, therefore, be possible to increase trap captures by combining sound with chemical attractants. The use of food material (with or without an added toxin) within the trap may increase retention as well.

It is envisioned that grandisoic acid would be effective in monitoring or controlling plum curculio populations when used in conjunction with any type of trap or pheromone dispenser as known in the art. Typically, the compound would be applied to the device in solution with hexane or other suitable carrier. Volatilization can be retarded by inclusion of an oleaginous extender such as trioctanoin in a amount of approximately 10% of the grandisoic acid solution. Slow release may also be effected by encapsulation or absorption into a porous substrate.

Under typical field conditions, about 0.1–10 mg of racemic grandisoic acid per dispenser or trap would be used to release the pheromone over a period of weeks. Of course, the greater the ratio of the (+)-(1R,2S) enantiomer to its antipode, the smaller the amount of pheromone that is needed.

The following examples are intended only to further illustrate the invention and are not intended to limit the scope of the invention which is defined by the claims.

EXAMPLE 1

Insects.

A laboratory culture of the southern non-diapausing strain of plum curculios was established from insects collected near Gainesville, Fla. Insects were reared on thinning apples (Amis). Insects representing the northern diapausing strain were collected in April through June near Peoria, Ill. Cotton boll weevils were obtained from a laboratory culture maintained at the USDA Boll Weevil Research Lab (Starkville, Miss.).

Collection and Isolation.

Volatiles were collected daily from individual unmated male and unmated female plum curculios feeding on apples or plums to detect sex-specific compounds using Super-Q® (Alltech Associates, Inc., Deerfield, Ill.) porous polymer filters. Volatile collections were pooled from males of the southern strain of plum curculios. The carboxylic acid was isolated by extraction with 5% $Na_2CO_3$; this basic extract was subsequently acidified with 10% HCl and extracted with n-hexane. Approximately 3 mg of grandisoic acid was isolated from 2000 male.day equivalents (southern strain) for an overall average of ca 1.5 µg per male.day. Similarly, volatiles were collected from males and females of the northern strain of plum curculios. Volatiles were also collected from unmated male cotton boll weevils feeding on cotton squares (var. DES-119) to provide a source of (+)-grandisol, (+)-(1R,2S)-1-methyl-2-(1-methylethenyl)-cyclobutaneethanol [2A].

Reduction of Grandisoic Acid to Grandisol.

The isolated grandisoic acid in hexane (ca. 10 µg in 1 ml) was treated with one drop of ($LiAlH_4$,1.0M in diethyl ether), neutralized with water and the hexane layer separated for analysis.

Racemic 1-methyl-2-(1-methylethenyl)-cyclobutaneacetic acid (grandisoic acid) [1].

A four gram sample of racemic 1-methyl-2-(1-methylethenyl)-cyclobutaneethanol (grandisol I) [2] (Bedoukian, Inc.) was oxidized to the corresponding racemic aldehyde, 1-methyl-2-(1-methylethenyl)-cyclobutaneacetaldehyde (grandisal) using pyridinium chlorochromate (Webster) (3.4 g, % yield 86.1). The racemic aldehyde was distilled under vacuum and a 3 gram sample was subsequently oxidized to racemic 1 using $AgNO_3$ and NaOH (Pickett): nearly colorless oil (1.23 g, % yield 32.2); eims m/z (rel. int. %) 168 (1), 125 (12), 109 (14), 108 (35), 93 (9), 91 (3), 81 (6), 79 (11), 77 (10), 69 (11), 68 (100), 67 (86), 55 (11), 53 (30), 43 (35), 41 (41); H NMR ($CDCl_3$) δ 2.61 (1H, m, H-2), 1.83 (1H, m, H-3a), 1.95 (1H, m, H-3b), 1.71 (1H, m, H-4a), 1.95 (1H, m, H-4b), 1.31 (3H, s, Me-5), 2.03 (1H, dd, J=14.6,H-6a), 2.54 (1H, d, J=14.6, H-6b), 4.85 (1H, m, H-9a), 4.65 (1H, m, H-9b), 1.64 (3H, s, Me-10); $^{13}C$ NMR ($CDCl_3$) δ 41.1 (C-1), 51.9 (C-2), 18.7 (C-3), 29.0 (C-4), 27.9 (C-5), 38.5 (C-6), 179.7 (C-7), 144.1 (C-8), 110.3 (C-9), 22.8 (C-10).

General Analytical Procedures.

Gas chromatography was performed using a Hewlett-Packard 5890 Series II GLC equipped with a flame ionization detector, and Hewlett-Packard 3396 Series II integrator. The columns used were a fused silica Durabond DB-5 (0.25-µm film thickness, 30 m×0.25 mm ID), a fused silica Durabond DB-1 (1.0-µm film thickness, 15 m×0.25 mm ID), and a fused silica Durabond CDX-B (chiral column, 0.25-µm film thickness, 30 m×0.25 mm ID) (J & W Scientific, Folsom, Calif.). For all analyses, the temperature program was: 50° C. initial temperature, 10° C./min to 250° C. with helium as the carrier gas. The injector and detector temperatures were 220° C. and 250° C., respectively. Injections of 1–2 µL were made in the splitless mode and changed to the split mode after 0.60 min. Retention indices were calculated relative to n-alkane standards (Poole). Electron impact mass spectra (ca. 100 ng sample) were obtained using a Hewlett-Packard 5970 Mass Selective Detector using an ionizing potential of 70 eV. Sample introduction was through a Hewlett-Packard 5890 GLC fitted with a DB-1 (0.25-µm film thickness, 15 m×0.25 mm ID) capillary column. Proton and carbon nuclear magnetic resonance spectra (ca. 200 µg sample) were obtained using frequencies of 400 and 100 MHZ, respectively with a Bruker ARX 400 instrument with $CDCl_3$ as the solvent. Shifts are reported in parts per million (δ) relative to tetramethylsilane. Optical rotation (ca. 3 mg sample) was measured using a Perkin-Elmer model 241 Polarimeter.

EXAMPLE 2

Field Bioassay.

Synthetic racemic grandisoic acid [1] was tested for attractancy in a mixed species orchard near Peoria, Ill., which had not been sprayed with pesticides for over ten years. The pheromone was blended with an equal part of mineral oil and 0.1% by weight 2,6-di-tert-butyl-4-methylphenol (BHT) as an antioxidant. The resultant blend was combined with Mirasperse® (pregelatinized corn starch passing 100 mesh screen; A. E. Staley, Decatur, Ill.) to yield ca. 8% (by weight) pheromone. Approximately 60 mg of the pheromone-oil-starch mixture was placed inside a piece of Teflon® tube (ca. 1.0 cm long×0.3 cm inside diam.) and the tube was subsequently sealed inside a polypropylene (4 mil) bag (ca. 2.5 cm×2.5 cm). The dispenser, commonly referred to as a "Baruch Bag" and containing ca. 5 mg. pheromone, was then inserted into the observation dome of a commercial boll weevil trap (Great Lakes IPM, Vestaburg, Mich.).

The experiment was set up as a paired test (baited vs unbaited traps, one trap per tree, with pairs of trees representing a single tree species and the trees not more than 10 m apart). There were 11 pairs of fruit trees in the experiment: 5 pairs of apples, 3 pairs of plums, 2 pairs of pears, and 1 pair of apricots. The treatments were randomly assigned to the trees of a pair. The traps were placed on the cut ends of branches which were as close to vertical as possible. The experiment extended from May 6 through September 29 (date last weevil was trapped), with traps being checked every 1–5 days throughout this period. The captured insects were counted and sexed. The total number of males and females captured for the entire trapping period was analyzed by a paired t-test after log (x+1) transformation using Statistix® 4.1 Analytical Software (Tallahassee, Fla.).

Traps baited with racemic 1 captured significantly (t=3.06, P=0.012, df=10) more female plum curculios than did unbaited traps; numerical means (n=11) were 3.45 and 1.27, respectively. Baited traps also captured significantly (t=2.79, p=0.019, df=10) more male plum curculios than did unbaited traps; numerical means (n=11) were 2.81 and 1.45, respectively. Therefore, racemic 1 has pheromonal activity, attracting both males and females. The capture of some weevils by control traps is not surprising, because plum curculios move within host trees principally by crawling (Owens) and reach fruit by walking rather than flying (LeBlanc).

There were obvious differences in the total number of plum curculios captured on the various tree species. The overall (baited plus unbaited, males plus females) mean number captured per trap for apple, plum, pear, and apricot were 4.0, 8.3, 1.5, and 1.5, respectively. The high number captured on plums is undoubtedly a reflection of its preference for this species (Quaintance).

It is understood that the foregoing detailed description is given merely by way of illustration and that modification and variations may be made therein without departing from the spirit and scope of the invention.

REFERENCES

Chapman, P. J. *New York St. Agric. Exp. Stn. Tech. Bull.* 1938, 684.

LeBlanc, J.-P. R.; Hill, S. B.; Paradis, R. O. *Environ. Entomol.* 1984, 13, 286–291.

Whalon, M. E.; Croft, B. A. *Ann. Rev. Entomol.* 1984, 29, 435–470.

Mayer, M. S.; McLaughlin, J. R. "*Handbook of Insect Pheromones and Sex Attractants*," CRC Press, Boca Raton, Fla., 1985.

Cross, W. H. *Annu. Rev. Entomol.* 1973, 18, 17–46.

Eller, F. J.; Bartelt, R. J.; Shasha, B. S.; Schuster, D. J.; Riley, D. G.; Stansly, P. A.; Mueller, T. F.; Shuler, K. D.; Johnson, B.; Davis, J. H.; Sutherland, C. A. *J. Chem. Ecol.* 1994, 20, 1537–1555.

Tumlinson, J. H.; Hardee, D. D.; Gueldner, R. C.; Thompson, A. C.; Hedin, P. A.; Minyard, J. P. *Science* 1969, 166, 1010–1012.

Hobbs, P. D.; Magnus, P. D. *J. Am. Chem. Soc. Chem. Comm.* 1974, 856–857.

Ayer, W. A.; Browne, L. M. *Can J. Chem.* 1974, 52, 1352–1360.

Mori, K.; Tamada, S.; Hedin, P. A. *Naturwissenschaften* 1978, 65, 653–654.

Zurfluh, R.; Dunham, L. L.; Spain, V. L.; Siddall, J. B. *J. Am. Chem. Soc.* 1970, 92, 425–427.

Mori, K.; Miyake, M. *Tetrahedron* 1978, 43, 2229–2239.

Owens, E. D.; Hauschild, K. I.; Hubbell, G. L.; Prokopy, R. J. *Ann. Entomol. Soc. Am.* 1982, 75, 357–362.

Padula, A. L.; Smith, E. H. *Ann. Entomol. Soc. Am.* 1971, 64, 665–668.

Quaintance, L.; Jenne, E. L. *U.S. Dept. Agric. Bur. Entomol. Bull.* 1912, 103.

LaFleur, G.; Hill, S. B. *J. Econ. Entomol.* 1987, 80, 1173–1187.

Prokopy, R. J.; Coli, W. M.; Hislop, R. G.; Hauschild, K. I. *J. Econ. Entomol.* 1980, 73, 529–535.

Vite, J.P.; Klimetzek, D.; Loskant, G. *Naturwissenschaften* 1976, 63, 582–583.

Light, D. M.; Birch, M. C. *Naturwissenschaften* 1979, 66, 159–160.

Hardee, D. D.; Wilson, N.M.; Mitchell, E. B.; Huddleson, P.M. *J. Econ. Entomol.* 1971 64, 1454–1456.

Dickens, J. C. *J. Chem. Ecol.* 1986, 12, 91–98.

Dickens, J. C. *Entomol. Exp. Appl.* 1989, 52, 191–203.

Booth, D. C.; Phillips, T. W.; Claesson, A.; Silverstein, R. M.; Lanier, G. N.; West, J. R. *J. Chem. Ecol.* 1983, 9, 1–12.

Blight, M. M.; Wadhams, L. J. *J. Chem. Ecol.* 1987, 13, 733–739.

Oehlschlager, A. C.; Pierce Jr., H. D.; Morgan, B.; Wilmalaratine, P. D. C.; Slessor, K. N.; King, G. G. S.; Gries, G.; Gries, R.; Borden, J. H.; Jiron, L. F.; Chinchilla, C. M.; Mexzan, R. G. *Naturwissenschaften* 1992, 79, 134–135.

Mampe, C. D.; Neunzig, H. H. *Ann. Entomol. Soc. Am.* 1966, 59, 614–615.

Hyder, D. E.; Oseto, C. Y. *J. Morphol.* 1989, 201, 69–84.

Harman, D. M.; Kransler, G. A. *Ann. Entomol. Soc. Am.* 1969, 62, 134–136.

Roseland, G. R.; Bates, M. B.; Oseto, C. Y. *Environ. Entomol.* 1990, 19, 1675–1680.

Poole, C. F.; Schuette, S. A. "*Contemporary Practice of Chromatography*," Elsevier, Amsterdam, 1984.

Amis, A. A.; Snow, J. W. In *Handbook of Insect Rearing*; Singh, P.; Moore, R. F., Ed.; Elsevier, Amsterdam, the Netherlands, 1985, Vol. I, pp. 227–235.

Webster, F. X.; Zeng, X.-N.; Silverstein, R. M. *J. Chem Ecol.* 1987, 13, 1725–1738.

Pickett, J. A.; Williams, I. H.; Martin, A. P.; Smith, M. C. *J. Chem. Ecol.* 1980, 6, 425–433.

I claim:

1. A method of attracting plum curculio weevils comprising applying to the habitat of said weevils an effective amount of 1-methyl-2-(1-methylethenyl)-cyclobutaneacetic acid.

2. The method of claim 1 wherein said 1-methyl-2-(1-methylethenyl)cyclobutaneacetic acid is a mixture of the 1R,2S and the 1S,2R enantiomers.

3. The method of claim 2 wherein the 1R,2S : 1S,2R enantiomeric ratio is at least 50:50.

4. The method of claim 2 wherein the 1R,2S and the 1S,2R enantiomers are in a racemic mixture.

5. The method of claim 1 wherein said 1-methyl-2-(1-methylethenyl)cyclobutaneacetic acid is exclusively the 1R,2S enantiomer.

6. An article comprising a pheromone dispenser and an amount of 1-methyl-2-(1-methylethenyl)cyclobutane-acetic acid effective for attracting plum curculio weevils.

7. The article of claim 6 wherein said 1-methyl-2-(1-methylethenyl)cyclobutaneacetic acid is a mixture of the 1R,2S and the 1S,2R enantiomers.

8. The article of claim 7 wherein the 1R,2S: 1S,2R enantiomeric ratio is at least 50:50.

9. The article of claim 7 wherein the 1R,2S and the 1S,2R enantiomers are in a racemic mixture.

10. The article of claim 6 wherein said 1-methyl-2-(1-methylethenyl)cyclobutaneacetic acid is exclusively the 1R,2S enantiomer.

* * * * *